United States Patent
Schoenle et al.

(10) Patent No.: US 10,429,305 B2
(45) Date of Patent: Oct. 1, 2019

(54) METHODS OF HIGH-RESOLUTION IMAGING A STRUCTURE OF A SAMPLE, THE STRUCTURE BEING MARKED WITH FLUORESCENCE MARKERS

(71) Applicant: Abberior Instruments GmbH, Goettingen (DE)

(72) Inventors: Andreas Schoenle, Goettingen (DE); Christian Wurm, Goettingen (DE); Benjamin Harke, Goettingen (DE); Gerald Donnert, Goettingen (DE)

(73) Assignee: ABBERIOR INSTRUMENTS GMBH, Goettingen (DE)

( * ) Notice: Subject to any disclaimer, the term of this patent is extended or adjusted under 35 U.S.C. 154(b) by 0 days.

(21) Appl. No.: 15/959,632

(22) Filed: Apr. 23, 2018

(65) Prior Publication Data
US 2018/0238804 A1  Aug. 23, 2018

Related U.S. Application Data

(63) Continuation of application No. PCT/EP2016/074763, filed on Oct. 14, 2016.

(30) Foreign Application Priority Data
Oct. 23, 2015 (EP) ..................... 15191304

(51) Int. Cl.
*G01N 21/64* (2006.01)
*G02B 21/00* (2006.01)

(52) U.S. Cl.
CPC ..... *G01N 21/6458* (2013.01); *G01N 21/6428* (2013.01); *G02B 21/0076* (2013.01)

(58) Field of Classification Search
CPC ........... G01N 21/6428; G01N 21/6458; G02B 21/0076
See application file for complete search history.

(56) References Cited

U.S. PATENT DOCUMENTS 8,399,857 B2 *  3/2013  Lippert .............. G01N 21/6458
                                                        250/461.1
2010/0208955 A1   8/2010  Mehes et al.
(Continued)

FOREIGN PATENT DOCUMENTS

EP    2 246 724 A1    11/2010
JP    2011-237616 A   11/2011

OTHER PUBLICATIONS

R. A. Hoebe et al: Controlled light-exposure microscopy reduces photobleaching and phototoxicity in fluorescence live-cell imaging, Nature Biotechnology, vol. 25, No. 2, Feb. 2007, pp. 249 to 253.
(Continued)

*Primary Examiner* — Dominic J Bologna
(74) *Attorney, Agent, or Firm* — Thomas | Horstemeyer, LLP

(57) ABSTRACT

In methods of high-resolution imaging a structure of a sample, the structure being marked with fluorescence markers, the sample is subjected to a light intensity distribution including an intensity maximum of focused fluorescence excitation light to selectively scan partial areas of interest of the sample. Fluorescence light emitted out of the sample is registered and allocated to a respective location of the light intensity distribution in the sample. The subjection of the sample to at least one part of the light intensity distribution is terminated at each location of the light intensity distribution, if at least one criterion of the following criteria is met: (a) a predetermined maximum light amount of the fluorescence light emitted out of the sample has been registered, and (b) a predetermined minimum light amount of the fluorescence light emitted out of the sample has not been registered within a predetermined period of time.

10 Claims, 8 Drawing Sheets

(56) References Cited

U.S. PATENT DOCUMENTS

| | | | |
|---|---|---|---|
| 2010/0214430 A1 | 8/2010 | De Boer et al. | |
| 2011/0036993 A1 | 2/2011 | Mano et al. | |
| 2012/0104279 A1* | 5/2012 | Reuss | G02B 21/0032 250/458.1 |
| 2012/0181936 A1 | 7/2012 | Jaffe et al. | |
| 2014/0029091 A1 | 1/2014 | Kleppe et al. | |
| 2014/0042340 A1* | 2/2014 | Hell | G01N 21/645 250/459.1 |
| 2015/0115176 A1 | 4/2015 | Watanabe et al. | |
| 2015/0308955 A1* | 10/2015 | Hell | G01N 21/6428 250/459.1 |
| 2017/0082844 A1* | 3/2017 | Hell | G02B 21/0036 |

OTHER PUBLICATIONS

T. Staudt et al.: Far-field optical nanoscopy with reduced number of state transition cycles, Optics Express vol. 19, No. 6 , Mar. 14, 2011, pp. 5644 to 5657.
International Preliminary Report on Patentability dated May 3, 2018 in co-pending, related PCT Application No. PCT/EP2016/074763.

* cited by examiner (a)

(b)

METHODS OF HIGH-RESOLUTION IMAGING A STRUCTURE OF A SAMPLE, THE STRUCTURE BEING MARKED WITH FLUORESCENCE MARKERS

CROSS REFERENCE TO RELATED APPLICATIONS

The present application is a continuation to international patent application PCT/EP2016/074763 filed on Oct. 14, 2016, entitled "Method and Apparatus for High-Resolution Imaging of a Structure of a Sample, which is Marked with Fluorescent Markers" and claiming priority to European patent application EP 15 191 304.3 filed on Oct. 23, 2015, entitled "Method and Device for High Precision Imaging of a Structure of a Sample Marked with Fluorescence Markers", to which the European patent EP 3 159 676 B1 has been granted on Apr. 4, 2018.

FIELD OF THE INVENTION

The invention relates to methods of high-resolution imaging a structure of a sample, the structure being marked with fluorescence markers, wherein the sample is subjected to a light intensity distribution including an intensity maximum of focused fluorescence excitation light, wherein partial areas of interest of the sample are scanned with the light intensity distribution, and wherein fluorescence light emitted out of the sample is registered and allocated to the respective location of the light intensity distribution.

Particularly, the present invention relates to such methods of high-resolution imaging in which the light intensity distribution with which the partial areas of interest of the sample are scanned comprises an intensity minimum of focused fluorescence inhibition light superimposed with the intensity maximum of the focused fluorescence excitation light, the intensity minimum being enclose by intensity maxima of the focused fluorescence inhibition light, so that the volume of the sample out of which the registered fluorescence light may origin is reduced in size by means of the fluorescence inhibition light. By means of the fluorescence inhibition light, the dimensions of this volume and thus the spatial resolution may, particularly, be reduced below the so-called diffraction barrier at the wavelength of the excitation light. The fluorescence inhibition light may inhibit the fluorescence of the fluorescence markers by which the structure of interest of the sample is marked in different ways, like for example by stimulated emission in STED fluorescence microscopy or by transferring the fluorescence markers into a dark state in which they are not able to fluoresce in RESOLFT fluorescence microscopy using switchable fluorophores.

In some embodiments, however, the present invention relates to methods of high-resolution imaging a structure of a sample in which no fluorescence inhibition light is used, like for example to confocal laser scanning fluorescence microscopy.

In all methods according to the invention, due to the subjection of the sample to the light intensity distribution, there is the danger that the sample is altered as a result of an influence of the light intensity distribution. An obvious alteration of the sample may be that the fluorescence markers, by which the structure to be imaged is marked, are bleached, i.e. permanently inactivated. The photochemical processes being the basis of bleaching the fluorescence markers may, however, also have an effect on other components of the sample. Particularly, living biological samples may be damaged or even devitalized due to the influence of the light intensity distribution.

The danger of the sample being altered due to the influence of the light intensity distribution increases with the light intensities in the light intensity distribution and the light dose to which the sample is subjected. In using fluorescence inhibition light which stimulates emission of fluorescence markers excited by the excitation light in STED fluorescence microscopy, the light intensities in the light intensity distribution are particularly high. Correspondingly, the dangers of undesired influences on the sample are also particularly high. On the other hand, STED fluorescence microscopy is suitable for imaging a structure marked with fluorescence markers in a sample within very short time which is of particular interest with altering structures of interest in a samples, particularly in living biological samples.

BACKGROUND OF THE INVENTION

A method of high-resolution imaging a structure of a sample, the structure being marked with fluorescence markers, wherein the sample is subjected to a light intensity distribution including an intensity maximum of focused fluorescence excitation light, wherein partial areas of interest of the sample are scanned with the light intensity distribution, wherein the fluorescence light emitted out of the sample is registered and allocated to the respective location of the light intensity distribution, and wherein the subjection of the sample to the light intensity distribution is terminated for the respective location, when a predetermined maximum light amount of the fluorescence light emitted out of the sample has been registered or even prior to that, if within a predetermined period of time a predetermined minimum light amount of the fluorescence light emitted out of the sample has not been registered, is known from R. A. Hoebe et al.: Controlled light-exposure microscopy reduces photobleaching and phototoxicity in fluorescence live-cell imaging, Nature Biotechnology, Volume 25, Number 2, February 2007, pages 249 to 253. By this known method, the subjection of the sample to the light intensity distribution is cut back as compared to a subjection over equal periods of time in all locations, everywhere where comparatively many fluorescence markers or no fluorescence markers are located in the sample. The light dose to which the sample is subjected for recording an image of the structure marked with the fluorescence markers may thus be considerably reduced. In the known method, the termination of the subjection of the sample to the light intensity distribution occurs due to controlling an acousto-optical modulator in the beam path of the fluorescence excitation light coming from a laser, the acousto-optical modulator being controlled depending on the light signal of a detector used for registering the fluorescence light.

R. A. Hoebe et al. also describe how the effect of the nevertheless occurring bleaching of the fluorescence markers may be corrected. For this purpose, the light dose to which the pixels of the sample have already been subjected is determined and used for correcting the intensity of the fluorescence light registered.

In a figure, Hoebe et al. document the cumulated light doses which have been received by each individual pixel in the focal plane after the entire volume of a sample has been scanned. In the figure, the different light doses are represented in false colors.

A method of high-resolution imaging a structure of a sample, the structure being marked with fluorescence markers, which is also designated as RESCue-STED is known from T. Staudt et al.: Far-field optical nanoscopy with reduced number of state transition cycles, Optics Express Vol. 19, No. 6, 14 Mar. 2011, pages 5644 to 5657. Here, the sample is subjected to a light intensity distribution in which an intensity maximum of focused fluorescence excitation light is superimposed with an intensity minimum of focused fluorescence inhibition light enclosed by intensity maxima of focused fluorescence inhibition light forming a donut. Parts of interest of the sample are scanned with the intensity minimum of the focused fluorescence inhibition light, and fluorescence light emitted out of the sample is registered and allocated to the location of the intensity minimum of the focused fluorescence inhibition light in the sample. The subjection of the sample to the light intensity distribution consisting of the focused fluorescence excitation light and the focused fluorescence inhibition light is terminated for the respective location of the intensity minimum of the focused fluorescence inhibition light, when a predetermined maximum light amount of the fluorescence light emitted out of the sample has been registered or when, even prior to that, a predetermined minimum light amount of the fluorescence light emitted out of the sample has not yet been registered within a predetermined period of time. In this way, the number of cycles of excitation and deexcitation which the fluorescence markers in the sample undergo in recording an image of the sample and thus the danger of bleaching the fluorescence markers are reduced.

T. Staudt et al. also describe an alternative way of implementing their RESCue strategy in which an upfront information with regard to the location of fluorescence markers is used to directly approach those coordinates at which a fluorescence inhibition is needed and to omit those locations at which fluorescence inhibition would be out of function. For example, it is proposed to at first record an image of lower resolution to obtain coarse information on the spatial structure and the density of features in the sample. Some features will then be rather isolated, and others will be densely packed. One may then (successively) apply a higher spatial resolution and concentrate on areas in which dense features are to be resolved. At the same time, coordinates may be omitted at which not objects are to be separated and at which, correspondingly, no switching off by fluorescence inhibition is necessary. The upfront information on the density of the fluorescence markers or the features may be obtained from the brightness of the initial image.

In both ways it is made possible to repeatedly image altering samples or to record images of the same sample along neighboring parallel sections.

In both known methods, the concentration of the fluorescence markers at the respective location of the sample is determined from the ratio of the measured light amount and the associated duration of subjecting the sample to the light intensity distribution, as this duration, in contrast to common laser scanning fluorescence microscopy in which the sample is subjected to the same light intensity distribution for a fixed period of time at each location, varies from location to location.

There still is a need of methods of high-resolution imaging a structure of a sample, the structure being marked with fluorescence markers, in which the light dose to which a sample is subjected for recording an image of a desired image quality may even be reduced further.

SUMMARY OF THE INVENTION

The present invention relates to a method of high-resolution imaging a structure of a sample, the structure being marked with fluorescence markers.

In a first embodiment, the method comprises superimposing an intensity maximum of focused fluorescence excitation light with an intensity minimum of focused fluorescence inhibition light, the intensity minimum being enclosed by intensity maxima of the focused fluorescence inhibition light, to form a light intensity distribution; subjecting the sample to the light intensity distribution; selectively scanning partial areas of interest of the sample with the intensity minimum of the focused fluorescence inhibition light of the light intensity distribution; registering fluorescence light emitted out of the sample and allocating the registered fluorescence light to a respective location of the intensity minimum of the focused fluorescence inhibition light of the light intensity distribution in the sample; and terminating subjecting the sample to at least the focused fluorescence inhibition light of the light intensity distribution at each location of the intensity minimum of the focused fluorescence inhibition light of the light intensity distribution, if at least one criterion selected from the following criteria is met for the respective location of the intensity minimum of the focused fluorescence inhibition light of the light intensity distribution. These criteria are a predetermined maximum light amount of the fluorescence light emitted out of the sample has been registered, and a predetermined minimum light amount of the fluorescence light emitted out of the sample has not been registered within a predetermined period of time. The sample is scanned with the focused fluorescence excitation light in steps, step sizes of the steps not being larger than dimensions of the intensity minimum of the focused fluorescence inhibition light, wherein the fluorescence light emitted out of the sample is registered and wherein the fluorescence inhibition light is only switched on after each of the steps, if a predetermined minimal light amount of the fluorescence light emitted out of the sample has been registered within a predetermined test period of time.

In a second embodiment, the method comprises superimposing an intensity maximum of focused fluorescence excitation light with an intensity minimum of focused fluorescence inhibition light, the intensity minimum being enclosed by intensity maxima of the focused fluorescence inhibition light, to form a light intensity distribution; subjecting the sample to the light intensity distribution; selectively scanning partial areas of interest of the sample with the intensity minimum of the focused fluorescence inhibition light of the light intensity distribution; registering fluorescence light emitted out of the sample and allocating the registered fluorescence light to a respective location of the intensity minimum of the focused fluorescence inhibition light of the light intensity distribution in the sample; and terminating subjecting the sample to at least the focused fluorescence inhibition light of the light intensity distribution at each location of the intensity minimum of the focused fluorescence inhibition light of the light intensity distribution, if at least one criterion selected from the following criteria is met for the respective location of the intensity minimum of the focused fluorescence inhibition light of the light intensity distribution. These criteria are a predetermined maximum light amount of the fluorescence light emitted out of the sample has been registered, and a predetermined minimum light amount of the fluorescence light emitted out of the sample has not been registered within a predetermined period of time. The partial areas of interest of the sample are selected in that the focused fluorescence excitation light is at first directed directly successively to partial areas of the sample which are located one behind the other in a scanning direction in scanning the sample, wherein fluorescence light emitted out of the sample is registered and wherein the partial areas of the sample are defined as partial areas of interest, if, within a predetermined test period of time, a predetermined minimal light amount of the fluorescence light emitted out of the sample has been registered. Afterwards, the sample is scanned over the partial areas of the sample arranged one after the other in the scanning direction, wherein subjecting the sample to at least the focused fluorescence inhibition light of the light intensity distribution only takes place in the partial areas of interest.

In a third embodiment, the method comprises subjecting the sample to a light intensity distribution including an intensity maximum of focused fluorescence excitation light; scanning partial areas of interest of the sample with the light intensity distribution; registering fluorescence light emitted out of the sample and allocating the registered fluorescence light to a respective location of the light intensity distribution in the sample; and terminating subjecting the sample to at least one part of the light intensity distribution at each location of the light intensity distribution in the sample if, within a predetermined period of time, a predetermined minimum light amount of the fluorescence light emitted out of the sample has not yet been registered. Subjecting the sample to the at least one part of the light intensity distribution is also terminated at each location of the light intensity distribution in the sample if, within at least one further period of time which is longer than the period of time, a further predetermined minimum light amount of the fluorescence light emitted out of the sample which is higher than the predetermined minimum light amount has not yet been registered.

In a fourth embodiment, the method comprises subjecting the sample to a light intensity distribution including an intensity maximum of focused fluorescence excitation light; scanning partial areas of interest of the sample with the light intensity distribution; registering fluorescence light emitted out of the sample and allocating the registered fluorescence light to a respective location of the light intensity distribution in the sample; and terminating subjecting the sample to at least one part of the light intensity distribution at each location of the light intensity distribution in the sample if at least one criterion selected from the following criteria is met for the respective location of the light intensity distribution. These criteria are a predetermined maximum light amount of the fluorescence light emitted out of the sample has been registered, and a predetermined minimum light amount of the fluorescence light emitted out of the sample has not been registered within a predetermined period of time. Over several repetitions of scanning the partial areas of interest or over several scanned x-y-planes of the sample having different z-positions, at least one of the predetermined maximum and minimum light amounts is reduced or the associated predetermined period of time is increased.

In a fifth embodiment, the method comprises subjecting the sample to a light intensity distribution including an intensity maximum of focused fluorescence excitation light; scanning partial areas of interest of the sample with the light intensity distribution; registering fluorescence light emitted out of the sample and allocating the registered fluorescence light to a respective location of the light intensity distribution in the sample; and terminating subjecting the sample to at least one part of the light intensity distribution at each location of the light intensity distribution in the sample if at least one criterion selected from the following criteria is met for the respective location of the light intensity distribution. These criteria are a predetermined maximum light amount of the fluorescence light emitted out of the sample has been registered, and a predetermined minimum light amount of the fluorescence light emitted out of the sample has not been registered within a predetermined period of time. A light dose which is saved due to terminating subjecting the sample to the at least one part of the light intensity distribution at the respective location or due to not subjecting partial areas of no interest of the sample to the light intensity distribution as compared to subjecting the sample to the light intensity distribution at all locations for a predetermined maximum period of time is determined and indicated.

Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
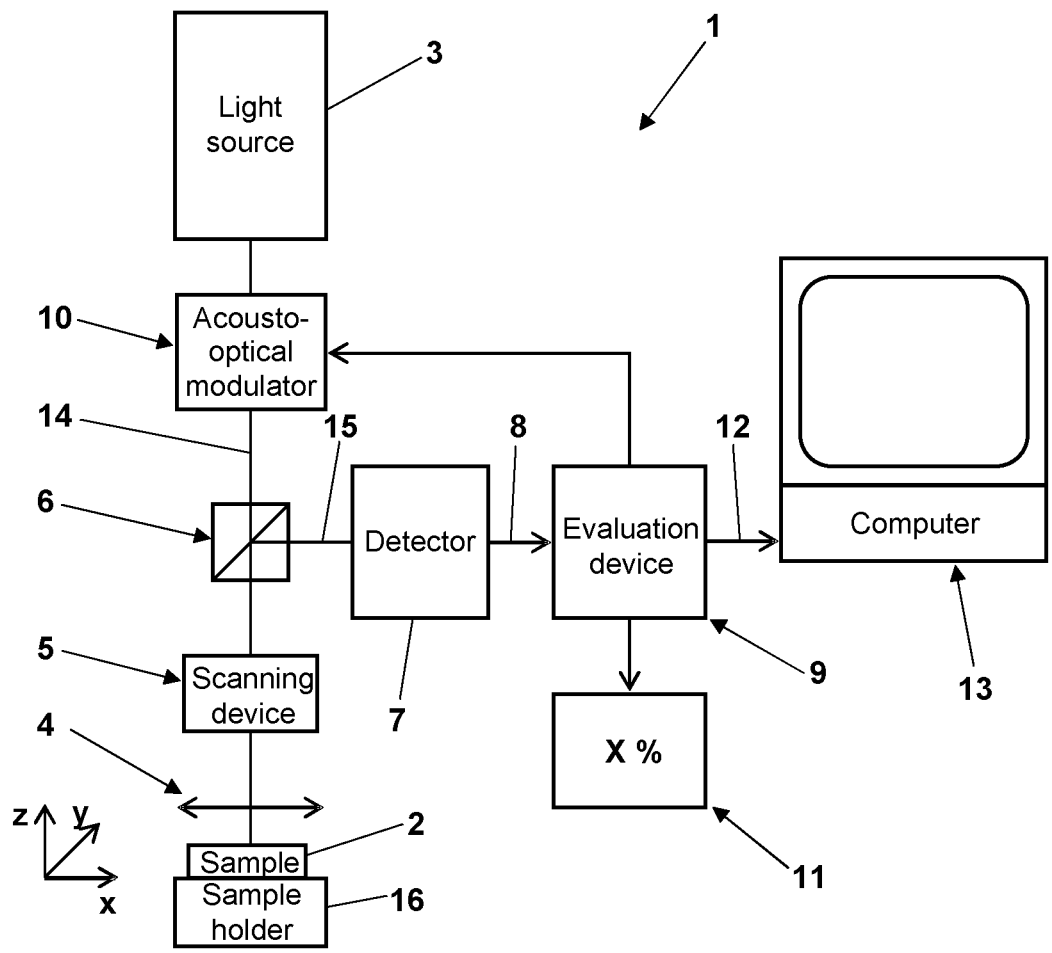
FIG. 1 is a schematic depiction of an apparatus for applying the method according to the invention.

In the first embodiment of the method according to the invention of high-resolution imaging a structure of a sample, the structure being marked with fluorescence markers, the sample is subjected to a light intensity distribution in which an intensity maximum of focused fluorescence excitation light is superimposed with an intensity minimum of focused fluorescence inhibition light enclosed by intensity maxima of the focused fluorescence inhibition light. The "fluorescence excitation light" will also be shortly designated as "excitation light" here. The plural used in "intensity maxima" shall expressively not exclude any partial light intensity distribution of the fluorescence inhibition light, in which the intensity minimum is enclosed by a ring-shaped intensity maximum. Such a light intensity distribution displays an intensity maximum on each side of the intensity minimum of the fluorescence inhibition light in each section along the optical axis.

In the first embodiment of the method according to the invention, partial areas of interest of the sample are selectively scanned with the intensity minimum of the focused fluorescence inhibition light, wherein the fluorescence light emitted out of the sample is registered and allocated to the respective location of the intensity minimum of the focused fluorescence inhibition light in the sample as a measure of the concentration of the fluorescence markers at the respective location. At least the subjection of the sample to the focused fluorescence inhibition light of the light intensity distribution is terminated at the respective location of the intensity minimum of the focused fluorescence inhibition light, when a predetermined maximum light amount of the fluorescence light emitted out of the sample has been registered, and/or when, within a predetermined period of time, a predetermined minimum light amount of the fluorescence light emitted out of the sample has not yet been registered. The "and/or" between said two criteria for terminating the subjection of the sample to at least one part of the light intensity distribution indicates that, in the first embodiment of the method according to the invention, the fluorescence light registered for the respective location is assessed either only for fulfilling the one criterion or fulfilling the other criterion or for fulfilling both criteria.

In the second embodiment of the method according to the invention, the partial areas of interest of the sample which are selectively scanned with the full light intensity distribution including the focused excitation light and the focused fluorescence inhibition light are selected in that focused fluorescence excitation light without fluorescence inhibition light is directed onto the sample, wherein fluorescence light emitted out of the sample is registered and wherein a partial area of the sample is defined as a partial area of interest, if for this partial area, within a predetermined test period of time, a predetermined minimal light amount of the fluorescence light emitted out of the sample has been registered. In other words, a partial area which is at first only subjected to the fluorescence excitation light is declared as a partial area of interest which is then subjected to the full light intensity distribution of excitation light and fluorescence inhibition light, if—at least without using the fluorescence inhibition light typically having a very high light intensity—a minimal fluorescence activity has been determined for this partial area. If this minimal fluorescence activity is not existent even without the fluorescence inhibition light, it will also not be existent with the light intensity distribution additionally including the fluorescence inhibition light. In so far there is no use in scanning the respective partial area with the minimum of the fluorescence inhibition light and to, thus, stress the surroundings of the intensity minimum of the fluorescence inhibition light with the high intensities of the intensity maxima of the fluorescence inhibition light. As a result, in the second embodiment of the method according to the invention, large areas of the sample will only be subjected to the fluorescence excitation light. The fluorescence inhibition light is completely reserved for the partial areas of interest of the sample, where the fluorescence inhibition light is needed for increasing the spatial resolution. The total light dose, with which the sample is stressed to record one image, may thus additionally be reduced considerably as compared to known methods.

In a first actual implementation of the second embodiment of the method according to the invention, the sample is scanned with the focused fluorescence excitation light in steps with step sizes adjusted to the dimensions of the intensity minimum of the focused fluorescence inhibition light, i.e. with step sizes not larger than the dimensions of the intensity minimum of the focused fluorescence inhibition light, wherein the fluorescence inhibition light is only switched on in each step if the predetermined minimal light amount of the fluorescence light emitted out of the sample has been emitted within the predetermined test period of time. In other words, in each pixel, i.e. at each location, the sample is at first only subjected to the fluorescence excitation light, and the fluorescence inhibition light is only switched on if any fluorescence activity caused by the fluorescence excitation light is registered at all. Otherwise, the fluorescence inhibition light is not switched on for the respective pixel, and the fluorescence excitation light may also be switched off until the next pixel, i.e. location, is reached.

In a second actual implementation of the second embodiment of the method according to the invention, the focused fluorescence excitation light without fluorescence inhibition light is directed, directly one after the other, to partial areas of the sample which are located one behind the other in a scanning direction in scanning the sample. Afterwards, the sample is scanned across these partial areas, wherein the sample is only subjected to the light intensity distribution including the fluorescence inhibition light in the partial areas of interest. In this implementation of the second embodiment of the method according to the invention, at first a line of the sample is scanned with the fluorescence excitation light only. Then, those sections of the line, in which fluorescence activity has been determined during the first scan, are scanned with the light intensity distribution including the fluorescence inhibition light, whereas at least the fluorescence inhibition light is suppressed for all other sections of the respective line. When afterwards scanning across the partial areas, the sample may be scanned in a plurality of lines arranged side by side along the scanning direction so that not every line of the fine raster used in scanning with the intensity minimum of the focused fluorescence inhibition light of the light intensity distribution is at first scanned with the non-delimited focused fluorescence excitation light to determine the partial areas of interest of the sample but, for example, only every second to tenth line of the fine raster.

The fluorescence excitation light used for selecting the partial areas of interest of the sample may be the same fluorescence excitation light, i.e. have the same wavelength, as the fluorescence excitation light which is superimposed with the fluorescence inhibition light in the light intensity distribution. It may, however, also be fluorescence excitation light of another wavelength by which other fluorescence markers, which appear together with the fluorescence markers excited by the other fluorescence excitation light, are excited for emission of fluorescence light. In this way, it is achieved that the fluorescence markers, which are later used in imaging the marked structure, are not yet stressed in any way in determining the partial areas of interest of the sample.

In the third embodiment of the method according to the invention of high-resolution imaging a structure of a sample, the structure being marked with fluorescence markers, which may be applied as a supplement to the first embodiment or to the second embodiment or to both the first and second embodiments or independently thereof, the sample is subjected to a light intensity distribution including a light intensity maximum of focused fluorescence excitation light, wherein partial areas of interest of the sample are scanned with the light intensity distribution, and wherein fluorescence light emitted out of the sample is registered and allocated to the respective location of the light intensity distribution. The subjection of the sample to at least one part of the light intensity distribution is terminated for the respective location if, within a predetermined period of time, a predetermined minimum light amount of the fluorescence light emitted out of the sample has not yet been achieved, or even later if within at least one predetermined further period of time which is longer than the period of time, a further predetermined minimum light amount of the fluorescence light emitted out of the sample, which is higher than the predetermined minimum light amount, has not yet been registered. In other words, with regard to whether it is worth to further subject the sample to the light intensity distribution and to, thus, further stress it at the respective location, a plurality of increasing threshold values which are assigned to a plurality of increasing periods of time are set or predetermined. In this way, the subjection of the sample to the light intensity distribution is not only terminated at the respective location, if, for example, within the first period of time no or very little fluorescence light has been registered, but also if the up to then registered fluorescence light has not yet been added up to a significant light amount within the longer second period of time. In this way as well, the total light dose to which the sample is subjected for recording one image of the structure is reduced further.

In the third embodiment of the method according to the invention, at least the subjection of the sample to a part of the light intensity distribution may also be terminated at the respective location of the sample if a predetermined maximum light amount of the fluorescence light emitted out of the sample has already been registered.

In the fourth embodiment of the method according to the invention of high resolution imaging a structure of a sample, the structure being marked with fluorescence markers, which may either be applied as a supplement to the first, second or third embodiment of the method according to the invention or independently thereof, the sample is subjected to a light intensity distribution including an intensity maximum of focused fluorescence excitation light, wherein areas of interest of the sample are scanned with the light intensity distribution and wherein fluorescence light emitted out of the sample is registered and allocated to the respective location of the light intensity distribution. At least the subjection of the sample to a part of the light intensity distribution is terminated at the respective location if a predetermined maximum light amount of the fluorescence light emitted out of the sample has been registered and—alternatively or additionally—if, within a predetermined period of time, a predetermined minimum light amount of the fluorescence light emitted out of the sample has not yet been registered. Over a plurality of repetitions of the scanning of the partial areas of interest, at least one of the predetermined maximum and/or minimum light amounts is reduced. In the method according to the invention, the light dose by which the sample is stressed for recording each image is kept small. In the area of the structure marked with the fluorescence markers, i.e. in the areas of interest, however, there is nevertheless a considerable photochemical stress to the fluorescence markers. This stress results in a more or less proportionate or percentaged bleaching during recording each image. This means that the structure is marked with a decreasing number of still active fluorescence markers. By means of reducing the predetermined maximum and/or minimum light amounts, it is cared for that the structure is nevertheless recognized in each image at a same level of security and that at the same time the potential of reducing the light dose is maximized. Similarly to repetitions of the scanning of the partial areas of interest, several parallel planes of the sample scanned one after the other, i.e. several parallel sections through the sample, and particularly several x-y-planes of the sample which have different z-position and which are scanned one after the other have an effect. Here, the light intensity distribution to which the sample has been subjected in recording the image of the one plane also has a bleaching effect on the fluorescence markers in the other planes. Thus, it is also suitable here to reduce at least one of the predetermined maximum and minimum light amounts.

As an alternative or additionally to reducing the minimum light amount, the associated predetermined period of time may be increased in the fourth embodiment of the method according to the invention. In any case, it is ensured by means of reducing the minimum light amount and/or by increasing the predetermined period of time that even a concentration of the fluorescence markers at the respective location of the intensity distribution which has been reduced by bleaching is securely acknowledged so that the subjection of the sample to the light intensity distribution is not prematurely terminated at the respective location of the sample.

Particularly, the respective maximum and/or minimum light amount may be reduced according to an exponential function and/or the predetermined period of time may be increased according to an exponential function. The exponent of the exponential function may be adjusted to the actual implementation conditions, i.e. to the fluorescence markers, particularly to their tendency to bleach, and to the composition and the absolute light intensities of the light intensity distribution. If these conditions remain constant, the exponent of the exponential function, as a rule, does not require a continuous adaptation but may also be kept constant.

In a fifth embodiment of the method according to the invention of high-resolution imaging a structure of a sample, the sample being marked with fluorescence markers, which may be applied alternatively or additionally to the first to fourth method according to the invention, the sample is subjected to a light intensity distribution including an intensity maximum of focused fluorescence excitation light, wherein partial areas of interest of the sample are scanned with the light intensity distribution and wherein fluorescence light emitted out of the sample is registered and allocated to the respective location of the intensity distribution, and wherein at least the subjection of the sample to a part of the light intensity distribution is terminated for the respective location, if a predetermined maximum light amount of the fluorescence light emitted out of the sample has been registered and—alternatively or additionally—if a predetermined minimum light amount of the fluorescence light emitted out of the sample has not yet been registered within a predetermined period of time. A light dose, which has been saved due to terminating the subjection of the sample to the at least one part of the light intensity distribution at the respective locations and/or by not subjecting partial areas of no interest of the sample to the light intensity distribution as compared to a subjection of the sample to the full light intensity distribution at each location for a fixed period of time, is terminated an indicated. The indication of the saved light dose makes it easier for the user of the fifth embodiment of the method according to the invention to optimize the method. This optimization has to be made with regard to a maximum image quality of the images recorded on the one hand and a minimum light dose to which the sample is subjected, i.e. a maximum saved light dose, on the other hand.

The light dose which is saved as compared to a subjection of the sample to the light intensity distribution for a fixed period of time at each location and which is indicated according to the fifth embodiment of the method according to the invention may be the light dose which has been saved over the last recorded image. Alternatively, it may be the light dose saved in a running time window, wherein the size of the running time window may be equal to the duration of recording one image; or it may be the total light dose saved since the beginning of the subjection of the sample to the light intensity distribution. Other settings of the period of time for which the saved light amount is indicated are also possible. Relatively short periods of time, preferably however of the duration of recording one image, are suitable to optimize the method, because the indicated value changes quicker with changed implementation conditions as compared to a case in which, for example, the light dose is indicated which has been saved since the beginning of the subjection of the sample. The saved light dose may, for example, be indicated as an absolute value or as a percentage of the light dose resulting from a subjection of the sample to the full light intensity distribution for a fixed period of time at each location.

In the third to fifth embodiment of the method according to the invention, the intensity maximum of the focused fluorescence excitation light may also be superimposed with an intensity minimum of focused fluorescence inhibition light enclosed by intensity maxima to form the light intensity distribution. If then at least the subjection of the sample to a part of the light intensity distribution is terminated at the respective location upon fulfilling certain criteria, this part of the light intensity distribution suitably is the focused fluorescence inhibition light.

By means of the focused fluorescence inhibition light, the spatial resolution in imaging the structure in the sample, which is marked with the fluorescence markers, is increased.

In all embodiments of the method according to the invention, the total light dose which has been saved by terminating the subjection of the sample to at least one part of the light intensity distribution at the respective location and/or by not subjecting partial areas of no interest of the sample to the light intensity distribution as compared to a subjection of the sample to the full light intensity distribution at all locations of the sample for a fixed period of time may be determined and optimized by adjusting at least one of the predetermined minimum and/or maximum light amounts and/or of the period of time associated with the minimum light amount. This optimization may be made manually or automatically based on predetermined optimization functions.

In all embodiments of the method according to the invention, at least one of the predetermined minimum and/or maximum light amounts and/or the period of time associated with the minimum light amount may be set dependently on how high a light power of the fluorescence light is which is registered at neighboring locations of the light intensity distribution, particularly at neighboring locations of the intensity minimum of the focused fluorescence inhibition light. The probability that two dark locations or two bright locations follow to each other is much higher than that a bright location follows to a dark location or vice versa. Correspondingly, it is less promising to wait for a certain light amount of fluorescence light at a new location neighboring a dark location than at a new location neighboring a bright location. This may be considered in setting the minimum and/or maximum light amounts as well as the associated periods of time to further optimize the saved light dose.

In the method according to the invention, the subjection of the sample to the light intensity distribution will not always be terminated at the respective location according to one of the criteria that the predetermined maximum light amount of the fluorescence light emitted out of the sample has been registered or that the predetermined minimum light amount of the fluorescence light emitted out of the sample has not yet been registered within the predetermined period of time. Then, termination of the subjection occurs due to the progression of the scanning of the sample with the light intensity distribution after a predetermined maximum period of time is over which corresponds to the maximum exposure of the respective location in the methods according to the invention. This maximum period of time is typically fixed. If it is chosen too short, the predetermined maximum light amount which corresponds to a desired signal-to-noise ratio is rarely achieved. If it is set too long, scanning the sample for recording one image takes unnecessarily long. In the method according to the invention, however, an excessive light dose to which the sample is subjected is avoided even with a too long maximum period of time. It may be advantageous to choose the predetermined maximum period of time so long that the predetermined maximum light amount is achieved as a rule, if the subjection of the sample to the light intensity distribution has not yet been terminated earlier, because the minimum light amount has not been achieved within the predetermined period of time. Then, the concentration of the fluorescence markers at the respective location may, as a rule, be determined with the desired signal-to-noise ratio from the period of time needed for achieving the maximum light amount.

In practice, the subjection of the sample to at least one part of the light intensity distribution may be terminated at the respective location in that the light intensity distribution or its respective part is shifted with regard to the sample, or in that the subjection of the sample to the light intensity distribution or to its respective part is terminated completely. Shifting the light intensity distribution with regard to the sample means an instant progression of the scanning of the sample to the next location. On the other hand, completely terminating the subjection of the sample to the light intensity distribution or to a part thereof means that the scanning of the sample does not yet proceed but that the sample is no longer subjected to the light intensity distribution or the part thereof at the respective location. Regardless of whether the subjection of the sample to the entire or only a part of the light intensity distribution is terminated, the detector may remain switched on for the remainder of the period of time until the scanning of the sample proceeds to the next location. If only a part of the light intensity distribution is terminated, the detector will detect further fluorescence light, the concentration of the fluorescence markers determined for the respective location, however, is zero or negligible if the minimum light amount has not yet been achieved during the associate period of time, or it is the quotient of the maximum light amount and the time needed for registering this maximum light amount. The total light amount registered by the detector at a location is only important if the subjection of the sample has not even been partially terminated for the respective location.

In the method according to the invention, a decision with regard to terminating the subjection of the sample to at least one part of the light intensity distribution at the respective location may be made by a logic programmed in a Field Programmable Gate Array (FPGA). The typical maximum period of time for which a pixel is exposed, i.e. the so-called pixel dwell time, typically is a in a range from several 100 nanoseconds up to several microseconds. This means that the decision with regard to the termination of the subjection to the at least one part of the light intensity distribution has to be made and implemented very quickly. A logic programmed in an FPGA may be helpful to achieve that.

An apparatus for implementing the method according to the invention of high-resolution imaging a structure of a sample, the structure being marked with fluorescence markers, may comprise light providing devices which include a light source and an objective lens and which provide a light intensity distribution including an intensity maximum of focused fluorescence excitation light. Further, the apparatus comprises scanning devices which scan the sample with the light intensity distribution, and detection devices which include the objective lens and a detector and which put out a light signal depending on a fluorescence light amount registered with the detector for a location of the light intensity distribution. Subjection termination devices of the apparatus terminate a subjection of the sample to at least one part of the light intensity distribution for the respective location depending on the light signal. These subjection termination devices are designed or configured for executing one of the methods according to the invention. Besides the subjection termination devices which may include at least one of a programmed FPGA and an acousto-optical modulator, the apparatus according to the invention may correspond to an STED fluorescence microscope, to an RESOLFT fluorescence microscope or any other laser scanning microscope.

Now referring in greater detail to the drawings, an apparatus 1 for high-resolution imaging of a structure of a sample 2, the structure being marked with fluorescence markers, is depicted in FIG. 1 and comprises light providing devices which include a light source 3 and an objective lens 4 and which provide a light intensity distribution having an intensity maximum of focused fluorescence excitation light 14. The sample 2 is subjected to this light intensity distribution. Scanning devices 5, which are also designated as a scanner, scan the sample 2 with the light intensity distribution in x- and y-directions. Detection devices, which include the objective lens 4, a dichroitic beam splitter 6 as a wavelength-selective beam deflection element and a detector 7, register fluorescence light 15 emitted out of the sample 2 and put out a light signal 8 which depends on the fluorescence light 15 registered for a respective location of the light intensity distribution. The light signal 8 is evaluated by evaluation devices 9. The evaluation devices 9 control subjection termination devices in form of an acousto-optical modulator 10 for terminating the subjection of the sample 2 to the light intensity distribution at the respective location when certain criteria are met. Additionally, the light dose saved due to this early termination of the subjection of the sample to the light intensity distribution is determined and indicated on indication devices 11 as a percentage of a fictive light dose, which would result if the sample 2 would be subjected to the full light intensity distribution at all locations for a fixed period of time. The images of the structure marked with the fluorescence markers, which are recorded by scanning the sample 2 with the light intensity distribution, are forwarded as image data 12 to a connected computer 13. Here, the image data 12, particularly the light amounts of the fluorescence light registered for the individual locations or pixels of the sample are corrected with regard to the exposure times of variable lengths due to the early termination of the subjection to the light intensity distribution. It is to be understood that the evaluation of the light signal 8 depends on the setting of the scanning devices 5. The scanning devices 5, however, typically scan the sample 2 according to a scheme independently on the light signal 8. In principle, it is, however, also possible to configure the scanning devices 5 such that they may serve as the subjection termination devices in that they shift the light intensity distribution with regard to the sample 2 to the next location every time the criteria for the termination of the subjection of the sample to the light intensity distribution are met for the present location. A sample holder 16 on which the sample 2 is supported may be movable in height, i.e. in the direction of the optical axis of the objective lens 4, to additionally scan the sample in z-direction.

Figure 2:
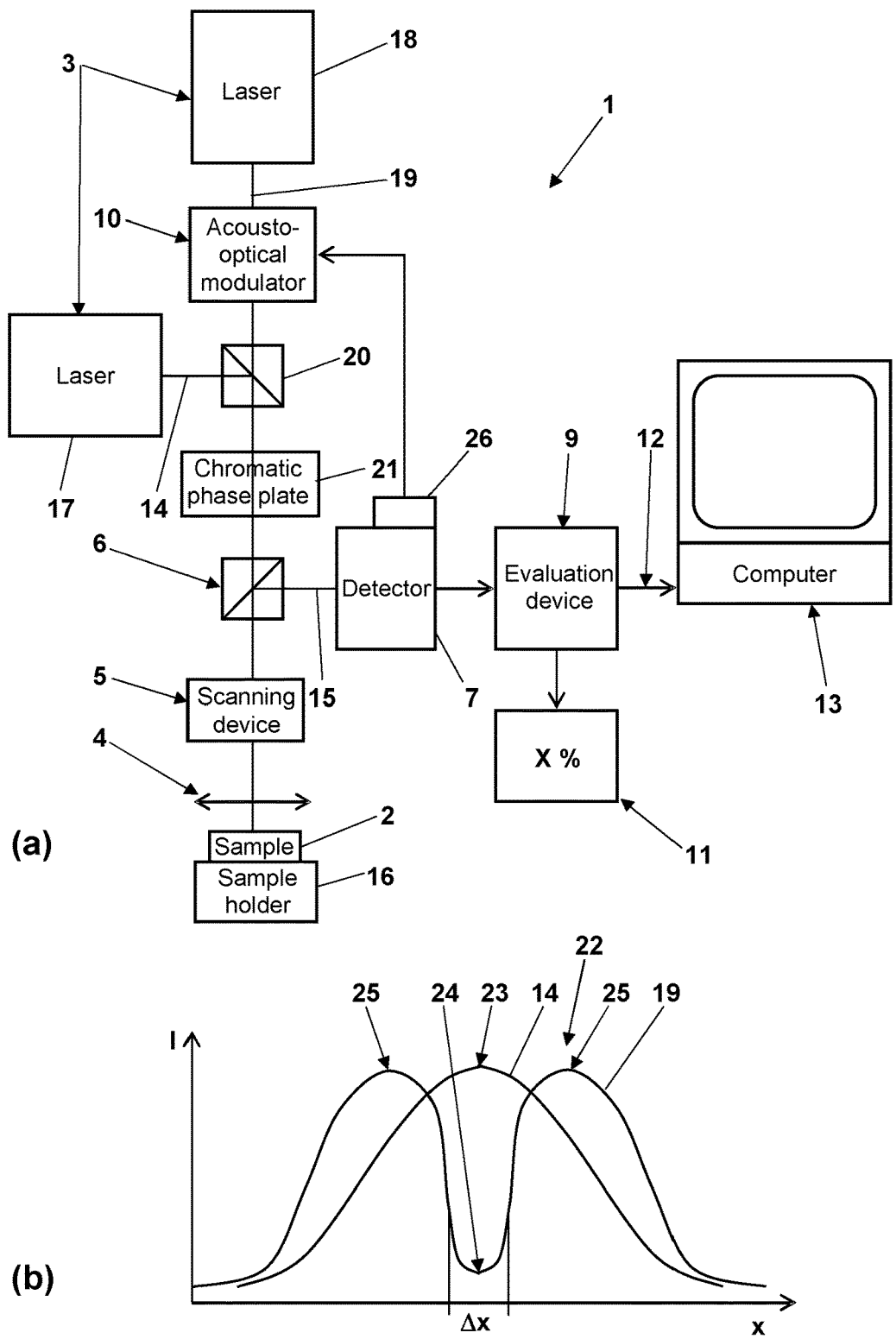
FIG. 2 is a schematic depiction of another apparatus for applying the method according to the invention.

The embodiment of the apparatus 1 for high-resolution imaging a structure of a sample 2, the structure being marked with fluorescence markers, according to FIG. 2 (a) comprises two lasers 17 and 18 for the excitation light 14 and for fluorescence inhibition light 19, respectively, as parts of the light source 3. By means of a polarization beam splitter 20, the excitation light 14 and the fluorescence inhibition light 19 are merged. By means of a chromatic phase plate 21, the phase fronts of the fluorescence inhibition light 19 are selectively deformed in such a way that the light intensity distribution 22 which is depicted in FIG. 2 (b) in a section results in the focus of the objective lens 4. The light intensity distribution 22 has superimposed partial light intensity distributions of the excitation light 14 and of the fluorescence inhibition light 19. At the location of the intensity maximum 23 of the excitation light 14, the fluorescence inhibition light 19 has an intensity minimum 24 which is enclosed by intensity maxima of the fluorescence inhibition light 19. In this way, the area out of which the fluorescence markers in the sample may emit the fluorescence light 15 is effectively restricted to an area Δx of the intensity minimum 14 in which the fluorescence inhibition light 19 does not inhibit the fluorescence. With this area Δx of the intensity minimum 24 of the fluorescence inhibition light 19, the sample 2 is scanned in the apparatus 1. The subjection of the sample 2 to the fluorescence inhibition light 19 which typically has a much higher intensity than the excitation light 14 and even a much higher intensity than indicated in FIG. 2 (b) is terminated by means of the acousto-optical modulator if certain criteria are met. By means of the acousto-optical modulator, it is also possible to direct the fluorescence inhibition light 19 to the respective location to the sample 2 only after the excitation light 14 as it will be described in the following in more detail. A control of the acousto-optical modulator 10 for terminating the subjection of the sample 2 to the fluorescence inhibition light 19 at the respective location is implemented by means of an FPGA 26 in which the criteria are programmed and which is associated with the detector 7. The FPGA particularly quickly responds to the criteria being met which is essential with scanning times or pixel dwell times of about a microsecond per location or pixel of the sample.

Figure 3:
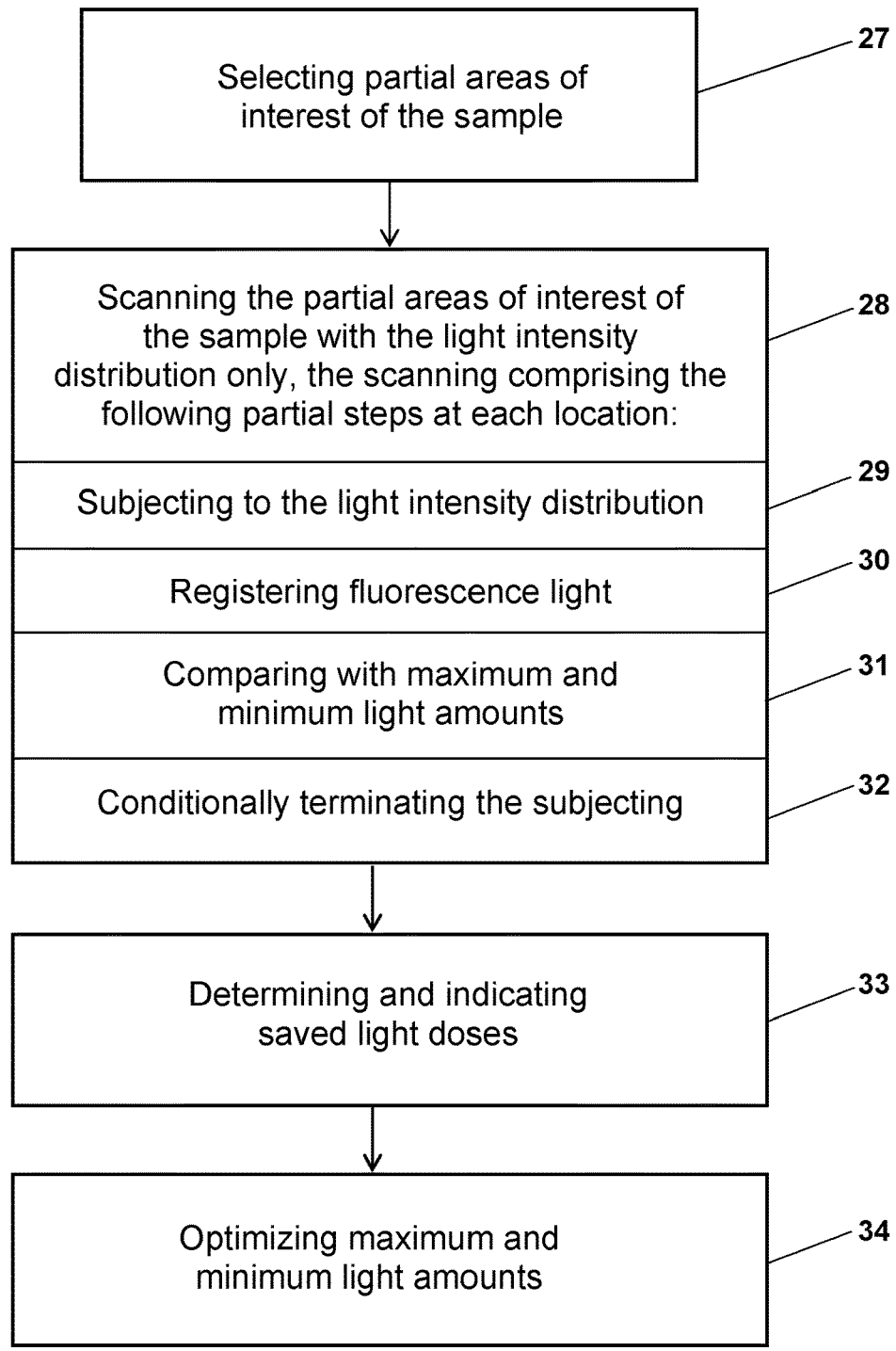
FIG. 3 is a block diagram of a method according to the invention including all five embodiments of the method according to the invention of high-resolution imaging a structure of a sample, the structure being marked with fluorescence markers.

The sequence of an embodiment of all methods according to the invention depicted in FIG. 3 as a block diagram starts with a step 27 of selecting partial areas of interest of the sample which are afterwards, in a step 28, scanned with the full light intensity distribution. Here, at each location of the sample, i.e. in each scanning step, the following partial steps are carried out. In a partial step 29, the sample is subjected to the full light intensity distribution. During a partial step 30, the fluorescence light emitted out of the sample which is caused by the light intensity distribution is registered. In a partial step 31, the registered fluorescence light 15 is compared to maximum and minimum light amounts. The minimum light amounts are associated with predetermined periods of time. Depending on the comparison, the subjection to at least one part of the light intensity distribution will be terminated in a partial step 32. By completely scanning the sample or the partial areas of interest of the sample, an image of the structure marked with the fluorescence markers is generated. In a step 33, the total light dose which has been saved over the sample 2 by early terminating the subjection to the full light intensity distribution as compared to equal exposure times for each location of the sample, i.e. as compared to a fixed effective pixel dwell time, is determined and indicated. For a maximization of the saved light dose while simultaneously achieving a desired image quality, the settings of the maximum and minimum light amounts as well of the associated periods of time are optimized in a following step 34. The step 34 may also include a successive reduction of the maximum and minimum light amounts and/or a successive increasing of the associated periods of time to compensate for a progressive reduction of the still active fluorescence markers in the partial areas of interest of the sample. Such a progressive reduction of the concentration of the fluorescence markers is a result of the subjection of these partial areas of the sample to the full light intensity distribution even if the subjection is as quickly terminated as possible in the method according to the invention.

Figure 4:
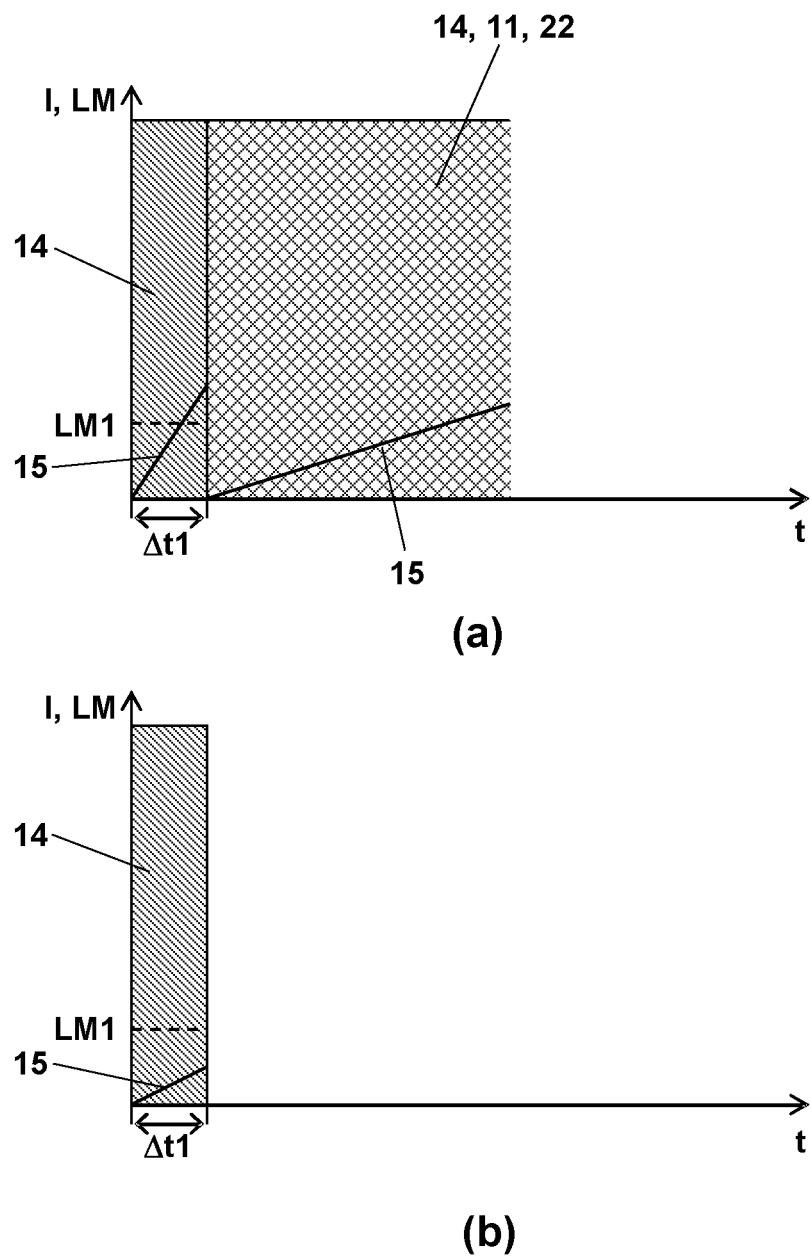
FIG. 4 illustrates a procedure in which a pixel of a sample is selected as a partial area of interest.

FIG. 4 illustrates an embodiment of executing the step 27 according to FIG. 3, i.e. of the selection of the partial areas of interest of the sample. At each location, the sample is at first only subjected to the excitation light 14 for a predetermined test period of time $\Delta t1$, and it is checked whether the light amount of the fluorescence light 15 registered within this test period of time $\Delta t1$ reaches a predetermined minimal light amount LM1. If this is the case, as indicated in FIG. 4 (*a*), the respective location is selected as a partial area of interest of the sample. If this is not the case, as illustrated in FIG. 4 (*b*), the respective location of the sample is not selected as a partial area of interest but as a partial area of no interest of the sample. At a location which has been selected as a partial area of interest of the sample the fluorescence inhibition light 19 may be added to the excitation light 14 as indicated in FIG. 4 (*a*). Then, the fluorescence light 15 emitted out of the sample which from now on may only origin from the spatial delimited area $\Delta x$ according to FIG. 2 (*b*) is registered starting from zero again. If, however, the respective location of the sample has not been determined as a partial area of interest, any further subjection to the excitation light 14 and/or to the fluorescence inhibition light 19 is avoided as depicted in FIG. 4 (*b*).

Figure 5:
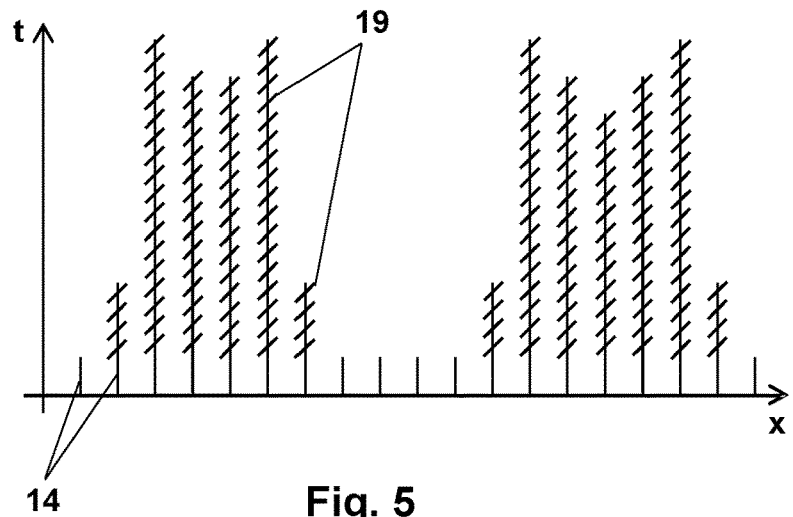
FIG. 5 illustrates how, in the procedure according to FIG. 4, different partial areas of the sample along a scanning line are selected as partial areas of interest.

For a line of locations or pixels of the sample running in x- or scanning direction, FIG. 5 shows the times for which the sample, at the individual locations or in the individual pixels, is subjected to the excitation light 14 and conditionally also to the fluorescence inhibition light indicated with oblique slashes. Here, the simultaneous subjection to the excitation light 14 and the fluorescence inhibition light 19 terminates after different periods of time which will be further explained in the following.

Figure 6:
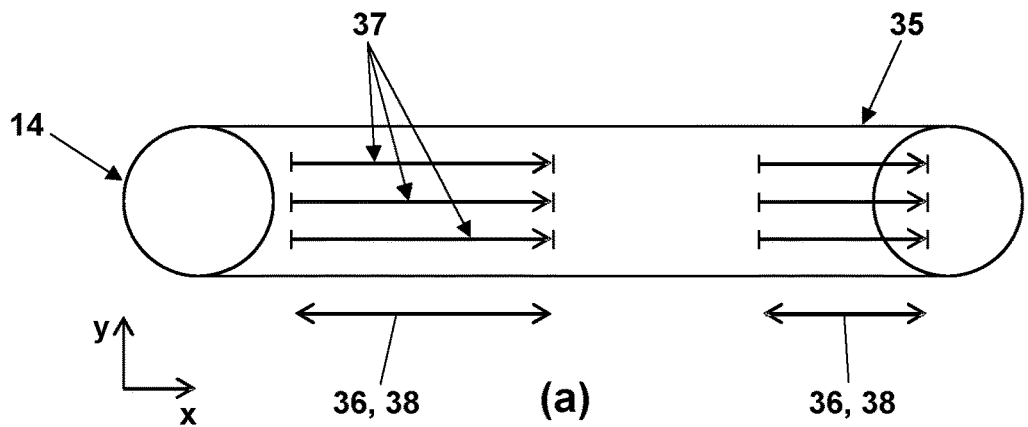
FIG. 6 illustrates another procedure how partial areas of interest are selected.
Figure 6:
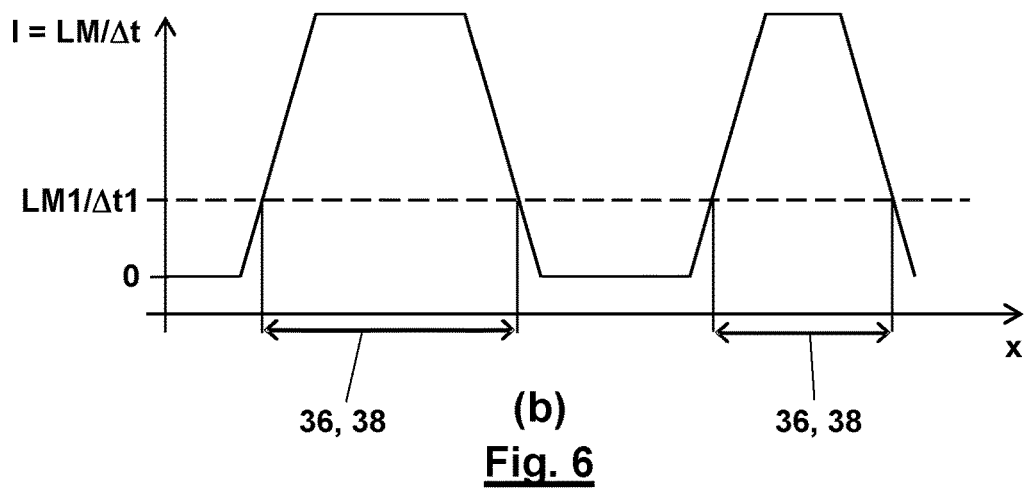

FIG. 6 illustrates an alternative embodiment of selecting the partial areas of interest of the sample in step 27 according to FIG. 3. Here, the sample is at first scanned along a line 35 running in x-direction with the focused excitation light 14 according to FIG. 6 (*a*). Assuming that an intensity I of the fluorescence light 15 results as illustrated in FIG. 6 (*b*), the sections 36 of the line 35 in which these intensities I exceed a quotient $LM1/\Delta t1$ of the predetermined minimal light amount LM1 and the predetermined test period of time $\Delta t1$ are selected as partial areas of interest of the sample. In these sections 36 the sample may then be scanned with the full light intensity distribution according to FIG. 2 (*b*) along lines 37 which are more densely arranged side by side than the width of the line 35 in scanning with the focused excitation light only.

Figure 7:
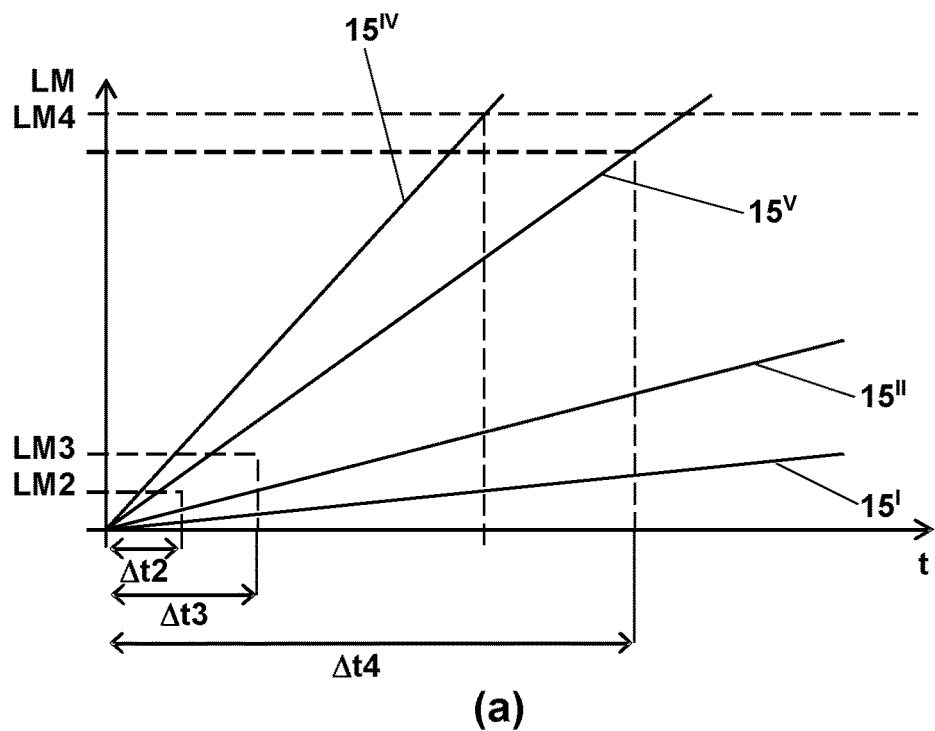
FIG. 7 illustrates criteria for terminating the subjection of the sample to a light intensity distribution at a location depending on an amount of fluorescence light registered for the location.
Figure 7:
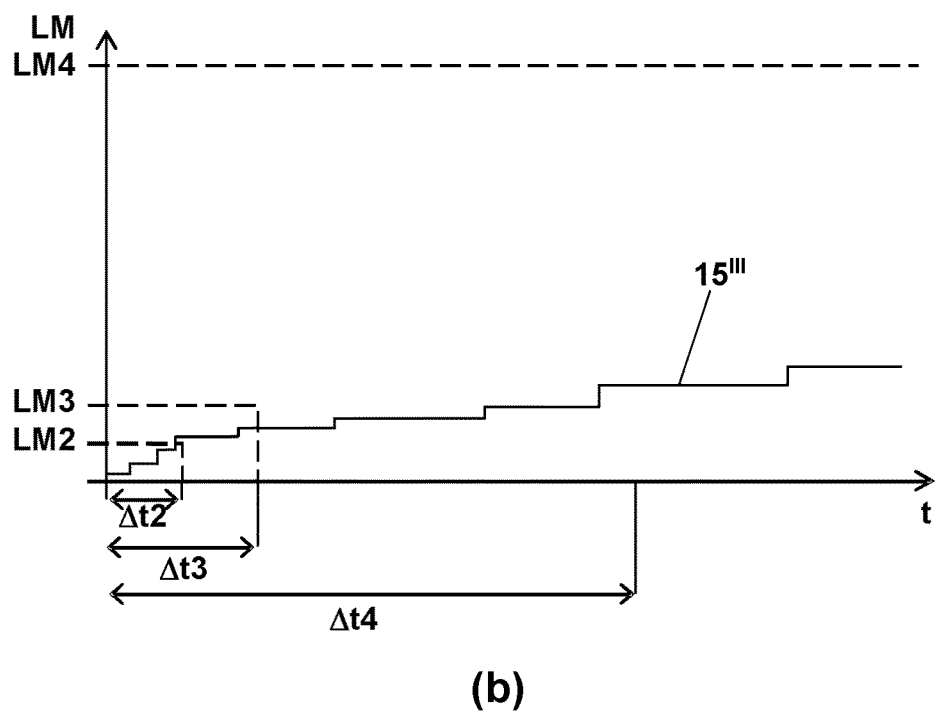

FIG. 7 illustrates the application of the criteria for the termination of the subjection of a location of the sample to the full light intensity distribution. This light intensity distribution may be a light intensity distribution including fluorescence inhibition light 19 according to FIG. 2 (*b*) or a light intensity distribution of excitation light 14 only. If the fluorescence light 15 emitted out of the sample and registered does not reach a predetermined minimum light amount LM2 within a predetermined period of time $\Delta t2$, the subjection of the sample to the light intensity distribution is terminated for this location. This is both the case if the registered fluorescence light 15' according to FIG. 7 (*a*) is only in a range of dark noise and if the fluorescence light 15" indicates fluorescence markers at the respective location of the sample but only at a sporadic level which is of no significance. The subjection of the sample to the light intensity distribution is also terminated at the respective location if, within a further predetermined period of time $\Delta t3$ a further predetermined minimum light amount LM3 is not achieved. This allows to acknowledge courses of the fluorescence light 15''', as depicted in FIG. 7 (*b*), as being of no interest, in which the predetermined minimum light amount LM2 has been reached within the predetermined period of time $\Delta t3$ but only randomly and not due to a uniformly high fluorescence activity at the respective location of the sample. Further, the subjection of the sample at the respective location is terminated if, prior to reaching a predetermined maximum period of time $\Delta t4$, a maximum light amount LM4 has been reached by the fluorescence light $15^{IV}$ as illustrated in FIG. 7 (*a*). Only if this maximum light amount LM4 is not reached up to the end of the maximum period of time $\Delta t4$, the sample is subjected to the light intensity distribution over the entire maximum period of time $\Delta t4$ at the respective location, and the light amount of the fluorescence light $15^V$ which is registered over this maximum period of time $\Delta t4$ is determined as indicated in FIG. 7 (*a*). It is to be understood that the measure of the concentration of the fluorescence markers at the respective location of the sample is the quotient of the light amount LM of the fluorescence light 15 divided by the associated period of time $\Delta t4$.

Figure 8:
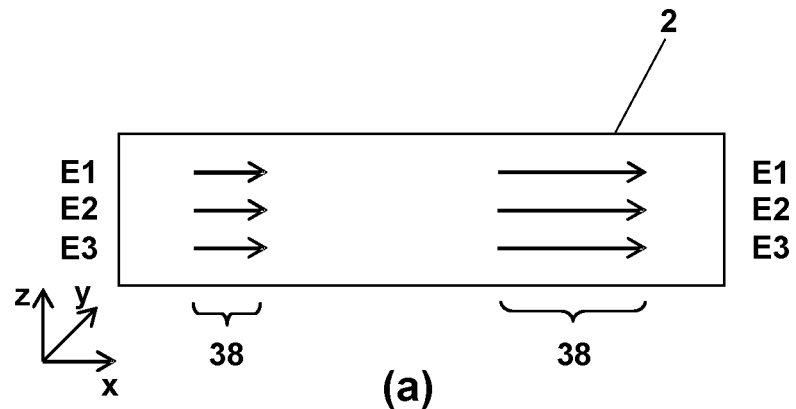
FIG. 8 illustrates an optimization of the termination criteria according to FIG. 7 in scanning the sample in several x-y planes staggered in z-direction.
Figure 8:
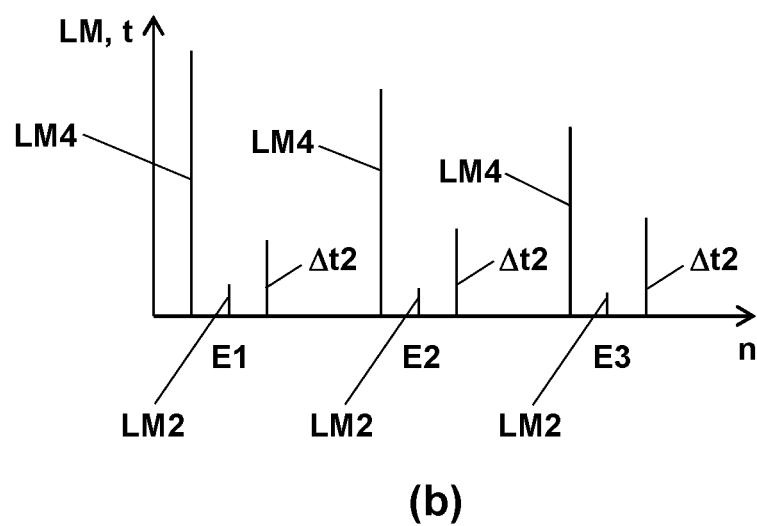

FIG. 8 (*a*) shows the sample 2 as it is successively scanned in areas 38 of interest along planes E1, E2 and E3 which are arranged at distances in z-direction. Here, the fluorescence markers in the subsequent planes are already subjected to the fluorescence inhibition light and thus partially bleached during scanning the previous neighboring planes. To compensate for this effect, the maximum light amount LM4 and the minimum light amount LM2 are reduced for the successively scanned planes E2 and E3 or the period of time $\Delta t2$ associated with the minimum light amount LM2 is increased as depicted in FIG. 8 (*b*).

Figure 9:
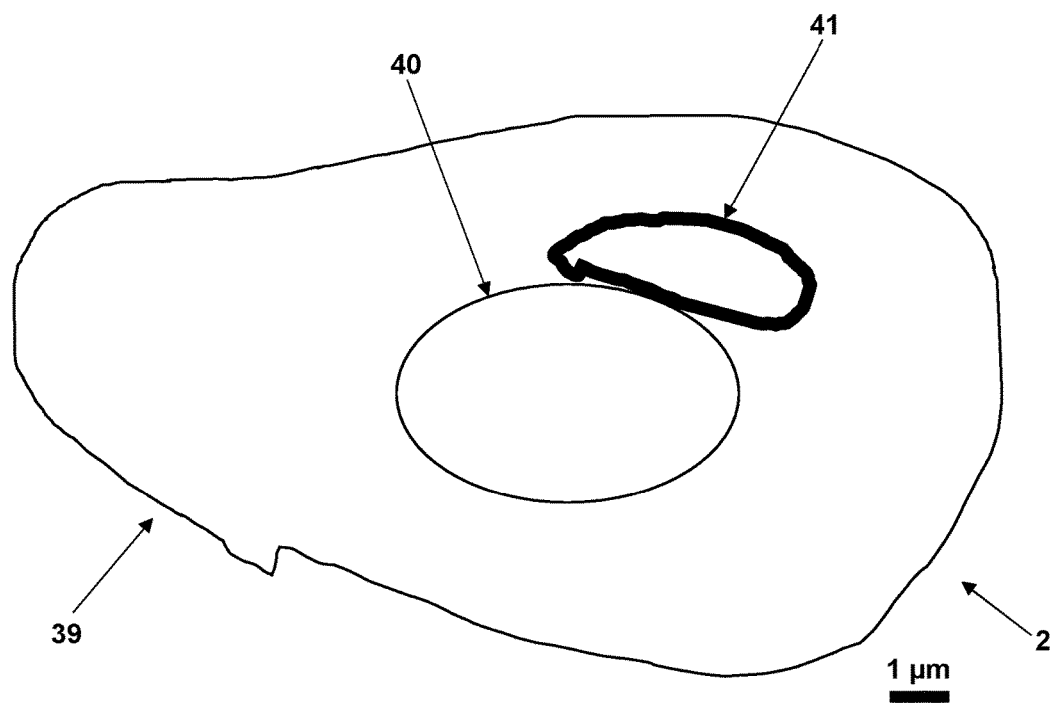
FIG. 9 illustrates a living cell as an example of a sample.

FIG. 9 depicts a cell 39 as an example of a sample 2 or a part of a sample 2. The cell 39 has a nucleus 40 and a structure 41 which is marked with fluorescence markers. According to the invention, only the area of the structure 41 is selected as an area of interest of the sample 2 and at least temporarily subjected to the full light intensity distribution. Other areas of the sample 2 are only subjected to the excitation light until it is determined that the minimal light amount LM1 is not achieved during the test period of time Δt1. That means that the light dose to which all areas of the sample 2, except of the areas of interest of the structure 41, are subjected to is only minimal.

Figure 10:
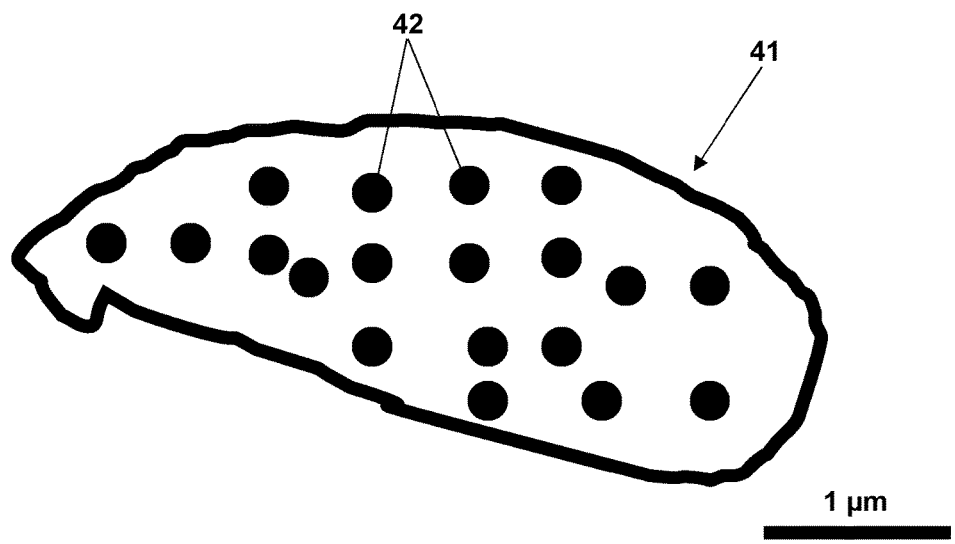
FIG. 10 shows a magnified structure of the cell according to FIG. 9, the structure being marked with fluorescence markers.

FIG. 10, at an enlarged scale, shows the area of the structure 41 in which certain proteins 42 are marked with fluorescence markers. In the area of the structure 41, the sample is subjected to the full light intensity distribution longer than Δt2 or Δt3 only at the locations of the proteins 42. Everywhere outside these locations, the subjection is quickly terminated, because the minimum light amount LM2 is not reached within the period of time Δt2 or the further minimum light amount LM3 is not reached within the further period of time Δt3. Even at the locations of the proteins 42 the sample is only rarely subjected to the full light intensity distribution for the full maximum period of time Δt4, because upon reaching the maximum light amount LM4 prior to the end of the maximum period of time Δt4 the subjection is terminated. The light dose to which the sample is subjected in the area of the structure 41 is thus clearly reduced even at the locations of the proteins 42 which are marked with the fluorescence markers. If the cell 39 according to FIG. 9 is a living cell, this living cell is only slightly affected in its biological activity by photochemical processes due to the influence of the light intensity distribution in imaging the sample according to the invention, particularly as the area of the core 40 of the cell 39 is only subjected to a minimum light dose which is necessary to acknowledge according to the present invention that it is no partial area of interest of the sample.

All methods according to the invention may also be carried out in parallel with several light intensity distributions, wherein the steps of the method according to the invention will then be carried out separately for each of the light intensity distribution.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of high-resolution imaging a structure of a sample, the structure being marked with fluorescence markers, the method comprising
   superimposing an intensity maximum of focused fluorescence excitation light with an intensity minimum of focused fluorescence inhibition light, the intensity minimum being enclosed by intensity maxima of the focused fluorescence inhibition light, to form a light intensity distribution,
   subjecting the sample to the light intensity distribution,
   selectively scanning partial areas of interest of the sample with the intensity minimum of the focused fluorescence inhibition light of the light intensity distribution,
   registering fluorescence light emitted out of the sample and allocating the registered fluorescence light to a respective location of the intensity minimum of the focused fluorescence inhibition light of the light intensity distribution in the sample, and
   terminating subjecting the sample to at least the focused fluorescence inhibition light of the light intensity distribution at each location of the intensity minimum of the focused fluorescence inhibition light of the light intensity distribution, if at least one criterion selected from the following criteria is met for the respective location of the intensity minimum of the focused fluorescence inhibition light of the light intensity distribution:
   a predetermined maximum light amount of the fluorescence light emitted out of the sample has been registered,
   a predetermined minimum light amount of the fluorescence light emitted out of the sample has not been registered within a predetermined period of time,
   wherein the partial areas of interest of the sample are selected in that the focused fluorescence excitation light is at first directed directly successively to partial areas of the sample which are located one behind the other in a scanning direction in scanning the sample, wherein fluorescence light emitted out of the sample is registered and wherein the partial areas of the sample are defined as partial areas of interest, if, within a predetermined test period of time, a predetermined minimal light amount of the fluorescence light emitted out of the sample has been registered, and
   wherein the sample is afterwards scanned over the partial areas of the sample arranged one after the other in the scanning direction, wherein subjecting the sample to at least the focused fluorescence inhibition light of the light intensity distribution only takes place in the partial areas of interest.

2. The method of claim 1, wherein a line of the sample is at first only scanned with the focused fluorescence excitation light and wherein, afterwards, sections of the line, for which, within the predetermined test period of time, the predetermined minimal light amount of the fluorescence light emitted out of the sample has been registered, are scanned with the light intensity distribution of the focused fluorescence excitation light superimposed with the fluorescence inhibition light, whereas at least the fluorescence inhibition light of the light intensity distribution is turned off for all other sections of the line.

3. The method of claim 2, wherein the sections of the line of the sample are scanned in several sublines running side by side in the scanning direction in scanning with the light intensity distribution of the focused fluorescence excitation light superimposed with the focused fluorescence inhibition light.

4. The method of claim 1, wherein the fluorescence excitation light used in selecting the partial areas of interest of the sample has another wavelength than the fluorescence excitation light which is superimposed with the fluorescence inhibition light in the light intensity distribution.

5. The method of claim 1, wherein a light dose which is saved due to terminating subjecting the sample to at least the focused fluorescence inhibition light of the light intensity distribution at the respective locations or by not subjecting partial areas of no interest of the sample to the light intensity distribution as compared to subjecting the sample to the light intensity distribution at each location for a predetermined maximum period of time is determined and optimized by adjusting at least one of the predetermined minimum and maximum light amounts or the associated predetermined periods of time.

6. The method of claim 1, wherein at least one of the predetermined minimum and maximum light amounts or the associated predetermined period of time is adjusted dependently on how high a light power of the fluorescence light registered for neighboring locations of the light intensity distribution is.

7. The method of claim 1, wherein subjecting the sample to the light intensity distribution is continued for the respective location for a predetermined maximum period of time, if subjecting at least the focused fluorescence inhibition light of the light intensity distribution is not terminated earlier.

8. The method of claim 1, wherein subjecting the sample to at least the focused fluorescence inhibition light of the light intensity distribution is terminated at the respective location in that the light intensity distribution is shifted with regard to the sample or in that subjecting the sample to at least the focused fluorescence inhibition light of the light intensity distribution is completely terminated.

9. The method of claim 8, wherein subjecting the sample to at least the focused fluorescence inhibition light of the light intensity distribution is terminated by controlling at least one acousto-optical modulator.

10. The method of claim 1, wherein a decision with regard to terminating subjecting the sample to at least the focused fluorescence inhibition light of the light intensity distribution is made by a logic programmed in an FPGA.

* * * * *